United States Patent [19]

Chen

[11] 3,998,859

[45] Dec. 21, 1976

[54] INTRODUCING $\Delta^{11}$ UNSATURATION INTO STEROID COMPOUNDS

[75] Inventor: Chin Hsin Chen, Rochester, N.Y.

[73] Assignee: Eastman Kodak Company, Rochester, N.Y.

[22] Filed: July 18, 1975

[21] Appl. No.: 597,119

[52] U.S. Cl. .......................... 260/397.1; 260/397.2
[51] Int. Cl.$^2$ ..................... C07J 7/00; C07J 9/00
[58] Field of Search ............................ 260/397.1

[56] References Cited

UNITED STATES PATENTS

| | | | |
|---|---|---|---|
| 3,164,616 | 1/1965 | Bharucha | 260/397.1 |
| 3,817,988 | 6/1974 | Barton et al. | 260/239.55 |
| 3,891,681 | 6/1975 | Saltzman | 260/397.1 |

Primary Examiner—Elbert L. Roberts
Attorney, Agent, or Firm—A. H. Rosenstein

[57] ABSTRACT

A process for the introduction of $\Delta^{11}$ unsaturation into steroid compounds having a C-12 sulfonate ester group is described. Dehydrosulfonation is carried out by reacting the sulfonate with a hexaalkylphosphoric triamide. The process is particularly useful with steroid compounds that also contain a blocked C-7 hydroxy group. The process yields the 11-enate in preference to the 6,11-dienate. The yield of the process can be increased by carrying out the reaction in the presence of a weak base.

15 Claims, No Drawings

3,998,859

INTRODUCING Δ¹¹ UNSATURATION INTO STEROID COMPOUNDS

BACKGROUND OF THE INVENTION

1. Field of the Invention

This invention relates to a process for preparing $\Delta^{11}$ steroid compounds from corresponding 12-hydroxy steroids. In a particular aspect, this invention relates to the introduction of $\Delta^{11}$ unsaturation into steroid compounds which are also substituted in the C-7 position. The process of this invention is particularly useful in the preparation of chenodeoxycholic acid from cholic acid.

2. Description of the Prior Art

Chenodeoxycholic acid has been found to be quite useful in the medical field and particularly in the treatment of gallstones. The major source of this acid is by synthesis from cholic acid. The prior art processes for this synthesis, however, involve complicated reaction sequences characterized by low yield and high cost. Due to the increased importance of chenodeoxycholic acid in the medical field and the quantities that are needed there exists a great need for an efficient, inexpensive process for its manufacture.

The production of chenodeoxycholic acid (CDC) from cholic acid involves the removal of the C-12 hydroxy group from the cholic acid without removing the C-7 hydroxy group. It is in this aspect that prior art processes for obtaining $\Delta^{11}$ unsaturation are unsatisfactory in the production of CDC. One such prior art process is described in U.S. Pat. No. 3,325,483 to Bharucha et al. In this process a 12-sulfonate steroid is dehydrosulfonated by treating with metal glycolates or salts of alkoxypolyethylene glycols to provide $\Delta^{11}$ unsaturation. However, in the synthesis of CDC, this process removes a large proportion of the C-7 substituent even when the substituent is blocked and the major product obtained is the 6,11-dienate. Thus only a small yield of the desired CDC is achieved. In U.S. Pat. No. 3,164,616 Bharucha describes a similar process wherein a strong metallic alkoxide base is used to treat the 12-sulfonate. However, this process yields only the unwanted 6,11-dienate and no 11-enate is formed.

There remains a great need for a high yield, inexpensive process for forming CDC to fill the necessary need for the materials for medical uses.

SUMMARY OF THE INVENTION

In accordance with the present invention, there is provided a process for the introduction of $\Delta^{11}$ unsaturation into steroid compounds having a C-12 sulfonate ester group comprising removal of the sulfonate ester group by treating the steroid compound with a hexaalkylphosphoric triamide. In a preferred embodiment the steroid compound also contains a blocked hydroxy group in the C-7 position. The blocked hydroxy group may be either axial or equatorial, although it is preferred that the group be in the axial direction. The process according to this invention selectively removes the sulfonate ester group without removing the blocked hydroxy group and thereby yields the 11-enate in preference to the 6,11-dienate. In another aspect of the invention, the yield of the process according to this invention can be increased by carrying out the reaction in the presence of a weak base.

The invention, and its advantages, will become more apparent in the detailed description of the preferred embodiments presented below.

DESCRIPTION OF THE PREFERRED EMBODIMENTS

The process of this invention is generally applicable in converting 12-hydroxy steroids to their $\Delta^{11}$ counterparts. The process of this invention is useful for example with derivatives of ergostane, cholestane, coprostane, sitostane, stigmastane, spirostane, cholane, allocholane, pregnane, allopregane, androstane, and testane. The process of this invention is particularly useful with 7,12-dihydroxy substituted steroids such as derivatives of cholic acid, glycocholic acid, taurocholic acid, and other bile acids.

The process of the present invention is shown below in Step 4 of the reaction sequence which illustrates the production of CDC from cholic acid.

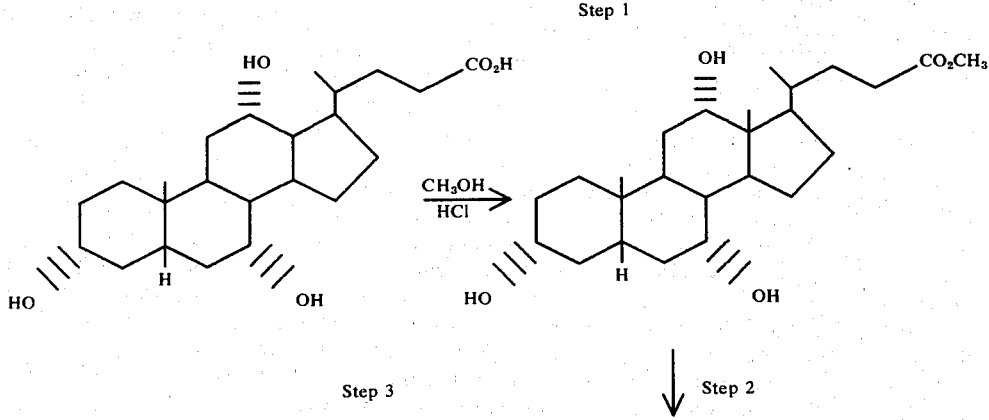

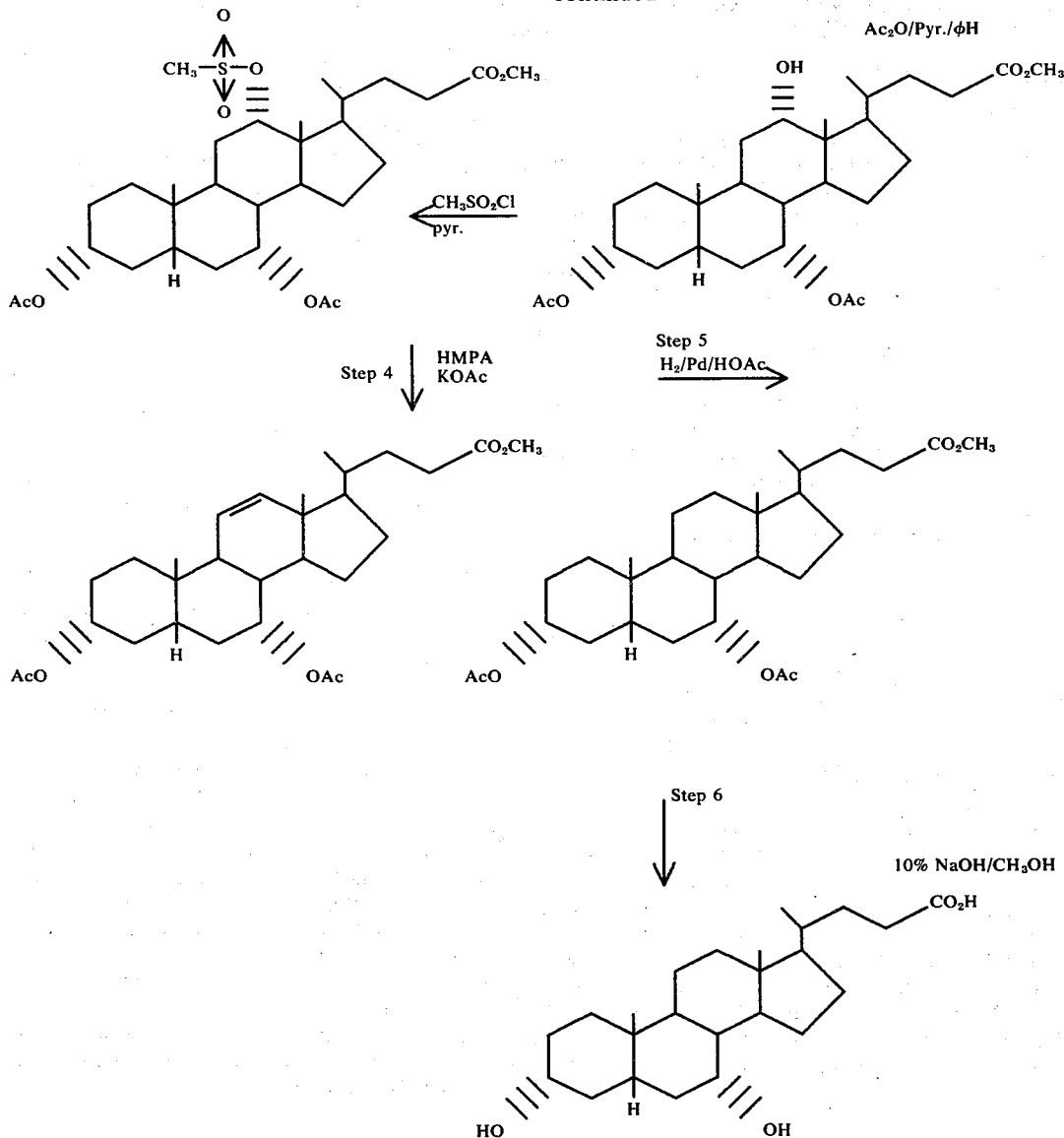

-continued

Step 1 is the esterification of the carboxylic C-24 acid group of the cholic acid to produce methyl cholate. This reaction is well known in the art and is used here to protect or block the acid group in the remaining steps. Step 2 is the selective protection or blocking by acetylation of the C-3 and C-7 hydroxyl groups of the methyl cholate by the reaction with acetic anhydride in pyridine and benzene thereby producing methyl 3,7-diacetyl cholate. This reaction is also well known and is described by Fieser and Rajagopalan *J. Amer. Chem. Soc.* 72, 5530, (1950). The disclosure of this article is hereby incorporated by reference. Step 3 is the sulfonation of the C-12 hydroxy group of the methyl 3,7-diacetyl cholate by methane sulfonyl chloride to produce methyl 3,7-diacetyl-12-mesylcholate. This reaction is described in the above-mentioned patents to Bharucha and Bharucha et al. (U.S. Pat. No. 3,325,483 and 3,164,616), the disclosure of which is also hereby incorporated by reference. Step 4 exemplifies the process of the present invention. The sulfonate derivative of the cholic acid (methyl 3,7-diacetyl-12-mesylcholate) is dehydrosulfonated by treating with hexamethylphosphoric triamide (HMPA). The major resulting product is the 11-enate derivative, methyl 3,7-diacetylchol-11-enate. Step 5 is the hydrogenation of the 11-enate over palladium black in acetic acid to produce methyl diacetyl chenodeoxycholate. Step 6 is the saponification of the methyl diacetyl chenodeoxycholate to regenerate the hydroxyl groups in the C-3 and C-7 positions. The end product is chenodeoxycholic acid as shown.

The process of this invention (as illustrated in Step 4) may be carried out with any of a variety of derivatives of steroid compounds. For instance, the nuclei of the steroid compounds may be substituted, or unsubstituted, saturated or unsaturated. As illustrated in the above reaction sequence, hydroxyl groups of the steroid molecule other than the C-12 hydroxy group may be protected or blocked by converting them into acyloxy groups or other similar protective groups known in the art, such as carbonates, succinates, benzoates, formates, and the like. The acid groups can also be blocked for example by esterification.

The process of the present invention is particularly useful where the 17-side chain of the steroid compound is —CH(CH₃)CH₂CH₂COOH,
—CH(CH₃)CH₂COOH,
CH(CH₃)COOH, -COOH, -COCH₃,
—CH₂CH₃, -CH(OH)CH₃,
—CH(CH₃)CH₂CH=C(C₆H₅)₂,
—CH(CH₃)CH₂CH₂CHOHR,
—C(CH₃)=CHCH=C(C₆H₅)₂ or
—C(CH₃)=C(C₆H₅)₂.

where R is alkyl preferably containing from 1 to 18 carbon atoms such as methyl, ethyl, propyl, isobutyl and the like or aryl such as phenyl, naphthyl, and substituted phenyls, such as halo, cyano or alkyl-substituted phenyls; and R¹ is hydrogen, lower alkyl containing from 1 to 6 carbon atoms, alkoxycarbonyl, aryl or cyano and R² is $-(CH_2)_n-$ where $n$ is 1 to 18.

The preferred sulfonate in the process of the present invention is the C-12 mesylate formed by sulfonating a C-12 hydroxy steroid with methanesulfonyl chloride. Other sulfonating agents that can be used in forming the starting material for the present invention include paratoluenesulfonyl chloride, benzenesulfonyl chloride, and chlorosulfonic acid. Frequently, where the starting material is also substituted in the C-7 position the mesylate is the only sulfonate that is sterically possible. Whenever the higher sulfonates can be prepared, the process of this invention is useful in dehydrosulfonation. C-7 blocked hydroxyl groups on the steroids described above include carbonates, succinates, benzoates, formates and the like.

Dehydrosulfonation is carried out by the reaction of the sulfonate with a hexaalkylphosphoric triamide dehydrosulfonating agent. The hexaalkylphosphoric triamide may be prepared by the reaction of phosphorus oxyhalide with a dialkylamine as described for example in U.S. Pat. No. 3,084,190 to Miller et al, the disclosure of which is hereby incorporated by reference. Due to steric hindrance in the reaction of the present invention, it is preferred that the alkyl portion of the hexaalkylphosphoric triamide be of from 1 to 3 carbon atoms although alkyls of greater than 3 carbon atoms can be used. Mixtures of hexaalkylphosphoric triamides are also useful and can be formed by reaction of the phosphorous oxyhalide with a mixture of dialkylamines. Useful hexalkylphosphoric triamides can be represented by the formula:

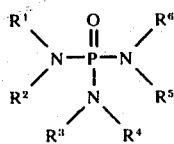

wherein each of R¹ through R⁶ is the same or different and is alkyl containing from 1 to 3 carbon atoms. Although not necessary in carrying out the process of this invention, it is preferred that the hexaalkylphosphoric triamide be purified prior to use. Impurities, such as unreacted phosphorus oxylate can be carried through the process and affect the purity of the final product. The hexaalkylphosphoric triamide is typically purified by redistillation or by other known methods. Useful hexaalkylphosphoric triamides include hexamethyl, hexaethyl, hexaisopropyl, hexa-n-propyl, and the like.

A byproduct of the reaction of the sulfonate with the hexaalkylphosphoric triamide is a sulfonic acid. The acid thus formed will catalyze and cause the elimination of acetate groups on the steroid derivative thereby reducing the yield of the desired product. In order to increase the yield, it is preferred to carry out the reaction of the present invention in the presence of a weak base to serve as a buffer and to neutralize the acid formed in the reaction. Weak bases useful in the practice of this invention include compounds having the general formula:

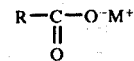

wherein R is selected from the group consisting of alkyl radicals of from 1 to 18 carbon atoms such as methyl, ethyl, isopropyl and the like and aryl radicals of from 6 to 12 carbon atoms, such as phenyl, naphthyl, biphenyl, phenoxy, and the like, and M is an alkali metal ion such as sodium, lithium or potassium. A particularly useful weak base is potassium acetate. Other weak bases such as sodium carbonate, lithium carbonate, sodium bicarbonate, potassium bicarbonate, and similar bases can also be used.

The concentration range of the reactants in the process of the present invention can vary over a wide range and is not critical. Practical considerations require that the reaction mixture be capable of being stirred. Where no weak base is present the weight ratio of hexaalkylphosphoric triamide to sulfonate is preferably between 10:1 to 1:1, more preferably between 10:1 to 3:1. If a weak base is used, the weight ratio of sulfonate to weak base can be between about 4:1 to about 1:1.

The useful temperature range for the process of the present invention is between 80° C and the decomposition temperature of the hexaalkylphosphoric triamide generally around 170° C. The preferred temperature range is between about 95° and 130° C. At about 95° C the reaction is complete in about 1 to 2 days. At about 130° C the reaction is complete in about 3 hours. As the temperature is increased, however, the yield generally goes down slightly. A typical yield for the process of the present invention at steam temperature (about 100° C) is about 84%.

The following examples are presented for a further understanding of the invention.

EXAMPLE 1

Preparation of Methyl Cholate (Step 1)

A mixture of 100 g cholic acid, 300 ml of methanol and 10 ml concentrated hydrochloric acid was refluxed on steam for 20 minutes. The resulting brown solution was refrigerated to induce crystallization. The crystals were collected, washed with 50 ml cold methanol, and dried to give 103 g methyl cholate, m.p. 153–154° C.

EXAMPLE 2

Preparation of Methyl 3,7-Diacetylcholate (Step 2)

A mixture of 102.5 g methyl cholate, 110 ml pyridine, 110 ml acetic anhydride and 440 ml benzene was stirred at ambient temperature for about 22 hours. The solution was poured into 500 ml distilled water and ice and the mixture was extracted with benzene. The benzene extracts were dried and evaporated in vacuo at ambient temperature. The resulting creamy solid was slurried with reagent ligroine, cooled briefly, filtered, washed with cold ligroine and air dried. The dry solid was recrystallized from 1 l. methanol and 700 ml distilled water to give 82 g of methyl 3,7-diacetylcholate, m.p. 182–184° C.

EXAMPLE 3

Preparation of Methyl 3,7-Diacetyl-12-mesylcholate (Step 3)

To a stirred ice-cooled solution of 50.7 g methyl 3,7-diacetylcholate in 150 ml of reagent dry pyridine under nitrogen was added dropwise 16 g methanesulfonyl chloride. Stirring was continued under nitrogen at ambient temperture for about 24 hours. Then the reaction mixture was poured into ice and water that had been saturated with sodium chloride. The resulting mixture was extracted with ether. The combined ethereal extracts were dried and concentrated in vacuo to a brown oil. This oil was extracted continuously under reflux with hexanes until only traces of gummy residue remained.

The partially crystallized hexane extract was cooled below 0° C and filtered to obtain methyl 3,7-diacetyl-12-mesylcholate in essentially quantitative yield, m.p. 85–88° C.

EXAMPLE 4

Preparation of Methyl 3,7-Diacetylchol-11-enate (Step 4)

A mixture of 10 g of methyl 3,7-diacetyl-12-mesylcholate, 40 g potassium acetate and 100 ml redistilled hexamethylphosphoric triamide (HMPA) was heated at about 100° C with stirring under a slow stream of nitrogen for about 2 days. Upon completion of the reaction, the reaction mixture was cooled and poured, with stirring, into about 1 liter of distilled water and ice. After coagulating, the white precipitate was filtered, washed with water and recrystallized from 125 ml methanol and water to give 7 g (84%) methyl 3,7-diacetylchol-11-enate; m.p. 137–139° C.

EXAMPLE 5

Preparation of Methyl Diacetylchenodeoxycholate (Step 5)

Methyl 3,7-diacetyl-11-cholenate (10.25 g) in 100 ml glacial acetic acid was conventionally hydrogenated over 500 mg palladium black. The catalyst was filtered off and the filtrate concentrated under reduced pressure. The resulting white solid was recrystallized in the same manner as that of Example 4 to give 9.88 g of methyl diacetylchenodeoxycholate, m.p. 125.5–127.5° C.

EXAMPLE 6

Preparation of Chenodeoxycholic Acid (Step 6)

A mixture of 5.1 g methyl diacetylchenodeoxycholate, 100 ml of 10% sodium hydroxide and 20 ml of methanol was refluxed for 15 hours. Traces of insoluble material were filtered out and the colorless filtrate was acidified with diluted sulfuric acid and ice. The fine white precipitate which form was collected, washed with distilled water until neutral, and air-dried.

Slow recrystallization from 150 ml ethyl acetate and 90 ml heptanes afforded 3.65 g of a first crop of crystalline chenodeoxycholic acid (CDC) (m.p. 138–142° C).

A second crop of CDC of 0.27 g (m.p. 137°–140° C) was crystallized by adding 700 ml reagent heptane to the mother liquor.

EXAMPLE 7

A mixture of 2 mg methyl 3,7-diacetyl-12-mesylcholate, and 0.2 ml HMPA was heated for 35 min. at 120–125° C and analyzed by gas chromatography. Although a large amount of the 6,11-dienate was obtained, some 11-enate was obtained without the use of a weak base.

EXAMPLE 8

This is a comparative example illustrating the result of using the process of Bharucha et al. U.S. Pat. No. 3,325,483 with a C-7, 12-dihydroxy steroid.

A mixture of 1 mg methyl 3,7-diacetyl-12-mesycholate and 0.1 ml dimethyl sulfoxide was heated on a steam bath for 1.5 hours and analyzed by gas chromatography. A major peak corresponding to the 6,11-dienate and a much smaller peak representing the 11-enate were observed. Less 11-enate was formed according to this procedure than was formed in Example 3 above. Thus the method according to the prior art patent could not efficiently produce chenodeoxycholic acid.

EXAMPLE 9

This is a comparative example illustrating the result of using the process of Bharucha U.S. Pat. No. 3,164,616 with a C-7-dihydroxy steroid.

A mixture of 10 mg methyl 3,7-diacetyl-12-mesylcholate, 10 mg potassium tert.-butoxide and about 0.5 ml dimethyl sulfoxide was heated on a steam bath for 2 hours and analyzed by thin layer chromatography. No starting material or 11-enate were observed. Similar results were obtained with a run carried out at room temperature. Thus using the process of U.S. Pat. No. 3,164,616 no chenodeoxycholic acid could be obtained.

The invention has been described in detail with particular reference to the preferred embodiments thereof, but it will be understood that variations and modifications can be effected within the spirit and scope of the invention.

I claim:

1. A process for providing $\Delta^{11}$ unsaturation in a steroid compound having a C-12 sulfonate ester group comprising removal of said sulfonate ester group by treating said steroid compound with a hexaalkylphosphoric triamide.

2. A process for providing $\Delta^{11}$ unsaturation in a steroid compound having a C-12 sulfonate ester group and a C-7 blocked hydroxy group comprising removal of said sulfonate ester group without the removal of said blocked hydroxy group by treating said steroid compound with a hexaalkylphosphoric triamide.

3. A process for providing $\Delta^{11}$ unsaturation in a steroid compound having a C-12 sulfonate ester group and a C-7 blocked hydroxy group comprising removal of said sulfonate ester group without the removal of said C-7 blocked hydroxy group by treating said steroid compound with a hexaalkylphosphoric triamide having the formula:

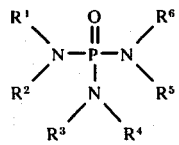

wherein each of R¹ through R⁶ is the same or different and is alkyl of from 1 to 3 carbon atoms, said process being carried out in the presence of a weak base.

4. The process of claim 3 wherein said weak base has the formula:

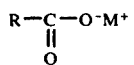

wherein R is selected from the group consisting of alkyl radicals of from 1 to 18 carbon atoms and aryl radicals of from 6 to 12 carbon atoms and M is an alkali metal ion.

5. The process of claim 1 wherein said steroid compound is a C-12 sulfonyloxy derivative of the cholane series.

6. The process of claim 1 wherein said hexaalkylphosphoric triamide is hexamethylphosphoric triamide.

7. The process of claim 1 wherein said steroid compound is methyl-3,7-diacetyl-12-mesylcholate and said hexaalkylphosphoric triamide is hexamethylphosphoric triamide.

8. The process of claim 3 wherein said steroid compound is methyl-3,7-diacetyl-12-mesylcholate; said hexaalkylphosphoric triamide is hexamethylphosphoric triamide and said weak base is potassium acetate.

9. The process of claim 1 wherein removal of the sulfonate ester group is carried out at a temperature of between 95° C and 130° C.

10. The process of claim 8 wherein the weight ratio of hexamethylphosphoric triamide to methyl-3,7-diacetyl-12-mesylcholate is from 10:1 to 3:1.

11. A process for providing $\Delta^{11}$ unsaturation in a steroid compound having C-7,12-hydroxy groups comprising: (1) sulfonating said steroid to produce a C-12 sulfonate ester group, and (2) dehydrosulfonating the sulfonate with a hexaalkylphosphoric triamide.

12. The process of claim 11 wherein said sulfonate is mesylate and the hexaalkylphosphoric triamide is hexamethylphosphoric triamide.

13. A process for preparing a steroid compound derivative of a C-12 hydroxy steroid comprising the steps of: (1) blocking of the acid groups, if any, of said steroid compound; (2) blocking of all but the C-12 hydroxy group, if any, in said steroid compound; (3) sulfonation of the C-12 hydroxy group of said steroid compound to produce the C-12 sulfonate; (4) dehydrosulfonation of said C-12 sulfonate by a hexaalkylphosphoric triamide to provide $\Delta^{11}$ unsaturation in said steroid compound; (5) hydrogenation to saturate said steroid compound; and (6) saponification of said steroid compound to regenerate acid groups of said steroid compound.

14. A process for preparing chenodeoxycholic acid from cholic acid comprising the steps of: (1) esterification of the acid group of the cholic acid to produce methyl cholate; (2) selective acetylation of the methyl cholate to produce methyl 3,7-diacetyl cholate; (3) mesylation of the methyl 3,7-diacetyl cholate to produce methyl 3,7-diacetyl-12-mesylcholate; (4) dehydromesylation of the methyl 3,7-diacetyl-12-mesylcholate by hexamethylphosphoric triamide in the presence of a weak base to produce methyl 3,7-diacetylchol-11-enate; (5) hydrogenation of the methyl 3,7-diacetylchol-11-enate to produce methyl diacetyl chenodeoxycholate; and (6) saponification of the methyl diacetyl chenodeoxycholate to produce chenodeoxycholic acid.

15. The process of claim 14 wherein the weak base is potassium acetate.

* * * * *